United States Patent
Steinwachs et al.

(10) Patent No.: US 9,095,354 B2
(45) Date of Patent: Aug. 4, 2015

(54) MEDICAL INSTRUMENT FOR CUTTING OFF TISSUE AND CARTILAGE FROM A HUMAN OR ANIMAL BODY

(71) Applicant: Karl Storz GmbH & Co. KG, Tuttlingen (DE)

(72) Inventors: Matthias Steinwachs, Herrliberg (CH); Sascha Berberich, Tuttlingen (DE)

(73) Assignee: KARL STORZ GMBH & CO. KG (DE)

( * ) Notice: Subject to any disclaimer, the term of this patent is extended or adjusted under 35 U.S.C. 154(b) by 119 days.

(21) Appl. No.: 13/862,097

(22) Filed: Apr. 12, 2013

(65) Prior Publication Data
US 2013/0274751 A1    Oct. 17, 2013

(30) Foreign Application Priority Data
Apr. 12, 2012  (DE) .......................... 10 2012 103 153

(51) Int. Cl.
| A61B 10/02 | (2006.01) |
|---|---|
| A61B 17/16 | (2006.01) |
| A61B 17/32 | (2006.01) |
| A61B 17/3207 | (2006.01) |
| A61B 17/00 | (2006.01) |

(52) U.S. Cl.
CPC ............ *A61B 17/16* (2013.01); *A61B 17/1604* (2013.01); *A61B 17/1659* (2013.01); *A61B 17/32002* (2013.01); *A61B 17/320708* (2013.01); *A61B 10/0266* (2013.01); *A61B 17/320758* (2013.01); *A61B 2017/00353* (2013.01); *A61B 2017/320024* (2013.01); *A61B 2017/320775* (2013.01)

(58) Field of Classification Search
CPC ........... A61B 10/0266; A61B 10/0275; A61B 2010/0225; A61B 17/16; A61B 17/1604; A61B 17/1631; A61B 17/1659; A61B 17/32002; A61B 17/320708; A61B 17/320758; A61B 17/320783; A61B 2017/320024; A61B 17/320775
USPC ............... 606/79, 83, 84, 160, 170, 174, 180, 606/184; 600/564–568, 570, 571
See application file for complete search history.

(56) References Cited

U.S. PATENT DOCUMENTS

| 4,811,734 | A | | 3/1989 | McGurk-Burleson et al. |
|---|---|---|---|---|
| 5,792,167 | A | | 8/1998 | Kablik et al. |
| 5,964,777 | A | * | 10/1999 | Drucker .................. 606/180 |
| 6,419,684 | B1 | * | 7/2002 | Heisler et al. ............ 606/170 |
| 6,610,059 | B1 | | 8/2003 | West, Jr. |

(Continued)

FOREIGN PATENT DOCUMENTS

| EP | 1882455 A1 | 1/2008 |
|---|---|---|
| WO | 2004037095 A2 | 5/2004 |

*Primary Examiner* — Michael T Schaper
(74) *Attorney, Agent, or Firm* — Whitmyer IP Group LLC

(57) ABSTRACT

A medical instrument serves for cutting off tissue and cartilage from a body. It comprises an outer shaft having at least a first window in a distal end area thereof. A hollow inner shaft is received within the outer shaft and can be rotated about a longitudinal axis of the outer shaft. The hollow inner shaft has at least one opening cooperating with the at least one window of the outer shaft in a cutting action when turning the inner hollow shaft. A further window is provided in the distal end area of the outer shaft which further window is surrounded by a curette having a separating edge. Tissue and cartilage separated by the curette can be cut into small pieces by the cutting edges of the rotatable inner shaft and then be sucked in through an opening of the inner hollow shaft.

13 Claims, 6 Drawing Sheets

(56) References Cited

U.S. PATENT DOCUMENTS

2008/0021488 A1* 1/2008 Berberich .................... 606/170
2008/0208194 A1* 8/2008 Bickenbach .................... 606/79
2011/0004120 A1* 1/2011 Drubetsky .................... 600/567
2013/0110147 A1* 5/2013 Dame .......................... 606/180

* cited by examiner

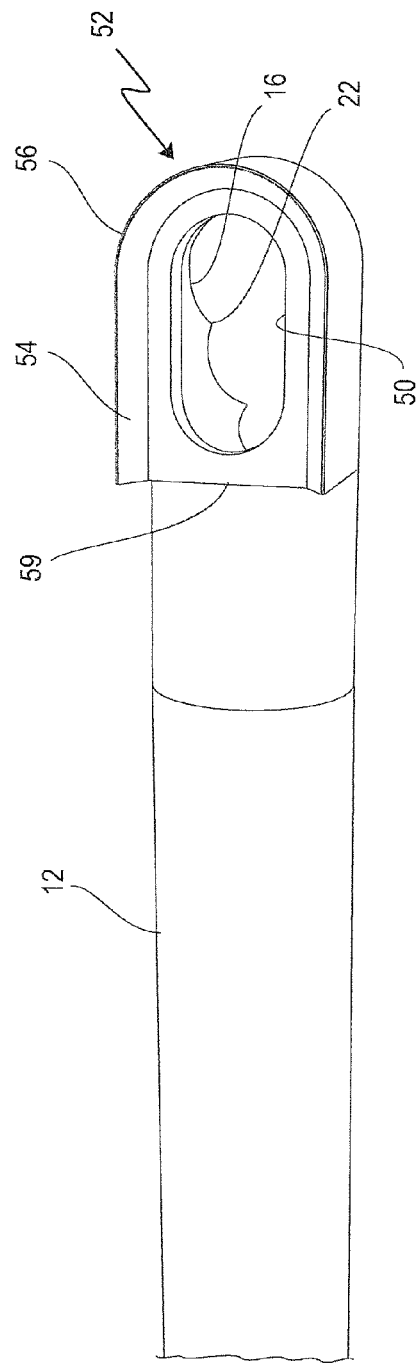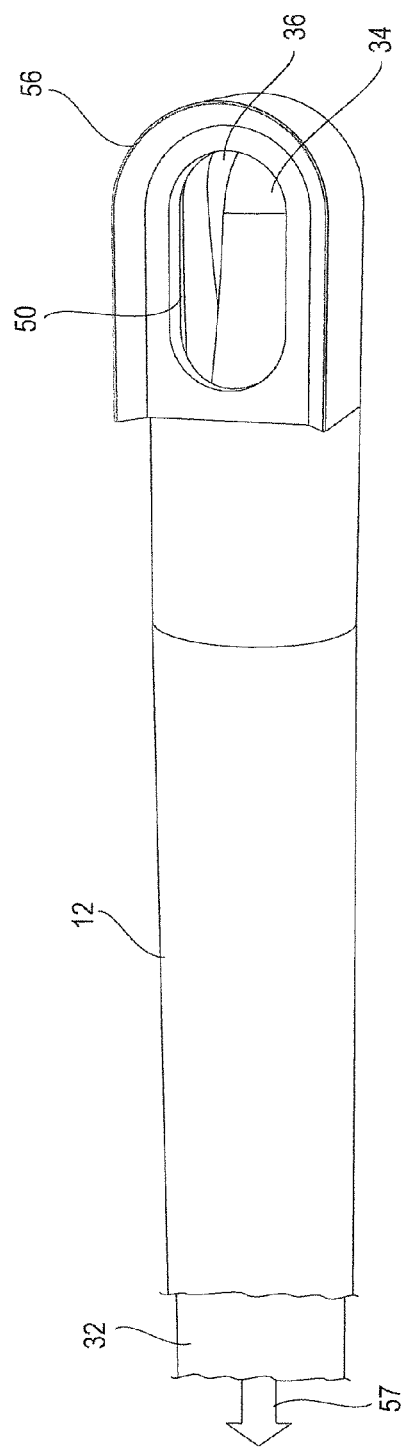

MEDICAL INSTRUMENT FOR CUTTING OFF TISSUE AND CARTILAGE FROM A HUMAN OR ANIMAL BODY

BACKGROUND OF THE INVENTION

The invention relates to a medical instrument for separating tissue and cartilage from a body.

One kind of such instruments, so-called shaver blades, is known from U.S. Pat. No. 4,811,734. For this purpose, the distal end of the outer shaft is guided to the operating site where the tissue that is to be separated is located. To separate the tissue, the inner shaft is moved in rotation by means of an external or internal drive. As they rotate, the cutting edges formed on the inner shaft cooperate in a cutting action with a border, designed as a cutting edge, of a window of the outer shaft. The cutting edge of an opening of the inner shaft runs past the cutting edge of the window in the outer shaft on each rotation. In order to ensure that the tissue to be separated is brought between the interacting cutting edges, the inner shaft can be connected to a vacuum source whose suction effect reaches through the inner shaft as far as the window on the outer shaft, in order to suck the tissue to be separated through the window into the shafts, such that the cutting edges can separate the tissue. By means of the vacuum, the separated tissue is sucked through the hollow inner shaft and thus carried away from the operating site.

Another kind of such instruments is a curette. Particularly in arthroscopy, relatively solid areas of cartilage lie below the cutaneous tissue and, in the event of cartilage defects, have to be removed down to the bone.

In autologous chondrocyte transplantation for the regeneration of cartilage, it is necessary for the defect margins to be extremely sharply defined. This is necessary in order to ensure that an implant placed on the defect site can fuse permanently onto these defect margins.

A curette is a shaft-like instrument which, at its distal end, has a laterally protruding peripheral separating edge. The contour and the size of the separating edge are chosen such that they can surround the defect site. The curette is penetrated into the cartilage tissue as far as the bone. The curette is provided centrally with an opening through which, by means of a spatula, the tissue and cartilage pieces that have been separated within the peripheral separating edge of the curette can be shaved off and removed. It is hard to avoid so-called debridement, i.e. where separated pieces of cartilage are released into the joint, which then necessitates irrigation of the joint in order to remove the small pieces, called chips. In the case of a relatively large defect site, the diameter of the curette is then correspondingly large.

Attempts have already been made to design a curette of this kind as a suction curette. However, the pieces of cartilage separated by the curette then always have to be smaller than the suction cross section of the instrument, since otherwise the suction cross section is blocked by the pieces of cartilage. Accordingly, the suction channel would then need to have a correspondingly large diameter, which is not feasible in defect sites with diameters of a few centimeters, since such a large amount of space is unavailable in operations on joints. Such a curette is known from WO 2004/037095 A2.

As already mentioned, these interventions are in most cases minimally invasive procedures. Two different instruments have to be brought to the operating site in succession, first a shaver blade, and then a curette, followed by irrigation of the joint.

It is object of the present invention to develop a medical instrument for separating tissue and cartilage, which instrument can be used more easily and more effectively to separate tissue and cartilage.

SUMMARY OF THE INVENTION

According to the invention, the object is achieved by a medical instrument comprising an outer shaft having a distal end and a proximal end, and having a longitudinal axis, said outer shaft having at least a first window in an area of said distal end, each of said first windows having at least one cutting edge; a hollow inner shaft received in that outer shaft, said hollow inner shaft being rotatable about said longitudinal axis, a proximal end of said hollow inner shaft can be attached to a vacuum source, said hollow inner shaft having, at its distal end area, at least one opening comprising at least one cutting edge cooperating with at least one of said cutting edges of said at least one first window of said outer shaft in a cutting action when turning said inner hollow shaft, thereby cutting off tissue and cartilage from a body, and wherein one further window is provided in said distal end area of said outer shaft, said further window being surrounded by a curette having a separating edge for separating tissue and cartilage from said body by penetrating said separating edge into said tissue or cartilage, and wherein said further window is in an area of at least one opening of said inner shaft allowing to cut tissue and cartilage separated by said separating edge of said curette into small pieces that can be sucked in through said at least one opening in said inner hollow shaft.

This measure now has the advantage that the instrument, at the distal end, is designed on one side as a shaver blade, by which the relatively soft tissue pieces can be separated, fragmented and sucked away. On the other side it is designed as a curette, which can be placed around a defect site and can be urged into the tissue, i.e. connective tissue and cartilage, as far as the bone. The pieces of tissue and cartilage that have been separated by the curette can be sucked through the further window at the outer shaft in the direction of the inner shaft and are there fragmented by the cutting edges of the rotating openings of the inner shaft. Thereafter, these fragmented pieces can be sucked into the interior of the inner shaft and carried off. The curette delimits an area that is substantially larger than the diameter of the inner shaft. But, no blockages occur, since the relatively large pieces of cartilage that have been separated through the curette are fragmented by the rotating inner shaft in the area of the further window into smaller pieces, and then the smaller pieces can be sucked through the small openings into the inner shaft. The separating edge of the curette can completely surround the area to be separated, and has sometimes the shape of a circle or an oval. But it can surround the area only partially or in several sections.

In the surgical intervention, the instrument is first of all placed with the area of the shaver blade window of the outer shaft at the defect site, and the softer parts of the connective tissue and cartilage are separated and sucked away. Thereafter, the instrument has to be turned around its longitudinal axis only until the curette comes to lie over the defect site. The separating edge of the curette is then urged into the cartilage tissue and separates the still remaining pieces of cartilage, particularly in the circumferential area within the curette. These pieces are likewise suctioned, fragmented and then carried off. It is also possible to use the instrument only as shaver blade or only as curette. Since the curette lies over the defect site and at least for the most part encloses the defect site, and since the separated pieces of cartilage are sucked in the direction of the rotating inner shaft, there is not the danger of pieces of cartilage being released into the joint and of the joint then having to be irrigated.

Thus, in addition to avoiding the use of two different devices that have to be pushed in one after the other and have to be removed one after the other from the operating site, it is also possible to dispense with irrigation of the bone.

If the cartilage parts are very small, for example in the case of a defect site in the knee, there is always the problem that the cartilage parts are not completely flushed away even in an irrigation procedure, and that they instead remain somewhere in the knee joint between the two adjoining bones of the upper leg and lower leg. The instrument is therefore easier to handle, and the procedures performed with it are much less traumatic for the patient and can be performed with a more reliable outcome.

Since parts of tissue or cartilage separated by the separating edge of the curette are divided by the openings of the rotating inner shaft into smaller pieces, the diameter of inner and outer shaft can be small in view of the width of the area surrounded by the curette. This allows to make the medical instrument with slender shafts but allows to treat relatively large areas with the curette.

In a further embodiment of the invention, the separating edge of the curette protrudes radially from an outer surface of the outer shaft.

This measure has the advantage that this embodiment corresponds to a conventional curette, such that the operator can therefore handle the instrument in the way to which he is accustomed when handling curettes as individual instruments. He can advance the instrument, mostly also with visual monitoring, to the defect site and, when he rotates the curette towards the operating site, he can place it in such a way that it correspondingly surrounds the defect site, and he can then move it laterally and urge it into the cartilage as far as the bone.

In another embodiment of the invention, the contour of the curette is U-shaped, when the outer shaft is viewed radially from the outside.

This measure has the advantage that, when the curette is placed on the defect site, it is still possible to look through an open side of the U into this inner area. This considerably facilitates handling, particularly placement on the defect site. It should be borne in mind that bone surfaces are strongly curved, particularly in the case of defect sites occurring commonly in the shoulder joint or knee joint. A U-shaped or horseshoe-shaped contour of this kind permits targeted placement on such a defect site.

In another embodiment of the invention, the open end of the U-shaped contour lies at the proximal side.

This measure has the advantage that the operator, when moving the instrument to the defect site from proximal to distal, has a view into the inner area of the curette via the open end at the proximal side and is thus able to place the curette at the target site.

Most curettes have a circular or oval, closed peripheral separating edge. Depending on the design and the field of application, the separating edge can lie in one plane or can be suitably curved.

In connection with the U-shaped structure, it is advantageous if the separating edge of the curette lies in one plane. Since the operator has a view through the open end of the U into the defect site, he can then also press the separating edge of the curette effectively into curved surfaces by means of suitable lateral tilting movements about the longitudinal axis of the shaft. Effectively means that a very straight cut edge is obtained at the circumference of the defect, which is an important precondition for good and rapid growth of tissue onto a corresponding implant.

In another embodiment of the invention, the separating edge of the curette protrudes radially by a height corresponding at least to the thickness of a layer of cartilage that is to be removed.

This measure has the advantage that the operator can press the curette sideways, and with force, into the sometimes very tough cartilage tissue, until he reaches the bone surface. This ensures that all of the cartilage can be separated. If this height corresponds to the usual layers of cartilage, it is also possible to prevent a situation where the separating edge is accidentally driven too far into the bone, which is undesirable.

In another embodiment of the invention, the outer shaft has a single window, which is arranged lying diametrically opposite the curette.

This has the advantage that, in relatively thin shafts, the single window of the shaver blade can then be made relatively large, such that the stability of the shaft in this distal end area is not so weakened by this window that deformations occur when driving in the curette. By virtue of the fact that the only one window lies diametrically opposite the curette, the material webs remaining between this one window of the shaver blade and the further window in the area of the curette are sufficient to maintain stability. Moreover, this gives the operator a clear sense that, after the first operating step with the shaver blade, he has to rotate the outer shaft through exactly 180° in order to then bring the curette ready for use to the defect site. This facilitates handling.

In another embodiment of the invention, the window of the shaver blade in the outer shaft is formed by an oblique cut, of the hollow outer shaft, that is inclined radially inwards in the proximal to distal direction.

This measure known per se has the advantage that, when starting to separate the relatively soft connective tissue, the distal end of the outer shaft can be placed parallel to this oblique cut, such that the inward rotating inner shaft can then effectively separate this connective tissue.

For this purpose, it is advantageous that the inner shaft protrudes from the window in the area of the oblique cut.

This permits particularly efficient separation of the connective tissue.

In another embodiment of the invention, the circumferential border of the window in the outer shaft has teeth standing vertically from this border.

This measure, likewise known per se, has the advantage that the instrument, in the area of the window in the outer shaft, can be pressed captively into the tissue by way of these teeth of the shaver blade.

In another embodiment of the invention, the rotatable inner shaft has a plurality of openings.

This measure, likewise known per se, has the advantage that the separated pieces of connective tissue and also the pieces of cartilage separated by the curette can be fragmented into very small parts by the plurality of windows, which can optionally also have different sizes and geometries, and these very small parts can then be easily sucked out through the inner shaft. In this way, the risk of the inner shaft becoming blocked by pieces of tissue or cartilage is eliminated.

It has proven particularly advantageous if three such openings are present in the inner shaft.

The plurality of openings can be distributed circumferentially on the inner shaft, most preferably at a same level.

In another embodiment of the invention, the outer shaft has, at the proximal end, a coupling piece through which the inner shaft can be guided from the proximal direction.

The coupling piece allows the outer shaft to be coupled to grip parts that can be gripped ergonomically by the hand of an operator. At the same time, this coupling piece serves as a guide for inserting the inner shaft into the outer shaft.

In another embodiment of the invention, the inner shaft has, at the proximal end, an attachment piece via which it can be connected to a vacuum source.

This measure has the advantage that, for the actual surgical procedure, a vacuum source can be attached, for example via a tube, to the inner shaft.

After a surgical procedure, this tube can be removed, such that the interior of the inner shaft can also be suitably cleaned.

In another embodiment of the invention, the attachment piece can be coupled by coupling elements to a drive which rotates the inner shaft about its longitudinal axis.

This measure has the advantage that, via these coupling elements, e.g. radially protruding coupling pins, it is possible to establish a connection to the drive which rotates the inner shaft.

It will be appreciated that the aforementioned features and the features still to be explained below can be used not only in the indicated combinations but also in other combinations or singly, without departing from the scope of the present invention.

BRIEF DESCRIPTION OF THE DRAWINGS

The invention is described and explained in more detail below on the basis of a selected illustrative embodiment and by reference to the attached drawings, in which:

FIG. 6 shows a likewise greatly enlarged perspective view of the distal end of the outer shaft in the area of the curette, without the inner shaft inserted, FIG. 7 shows a view comparable to FIG. 6 with the inner shaft inserted.

DETAILED DESCRIPTION OF A PREFERRED EMBODIMENT

A medical instrument according to the invention shown in FIGS. 1 to 7, and used for separating tissue and cartilage, is designated in its entirety by the reference number 10.

The instrument 10 has an elongate, rectilinear hollow outer shaft 12.

Figure 3:
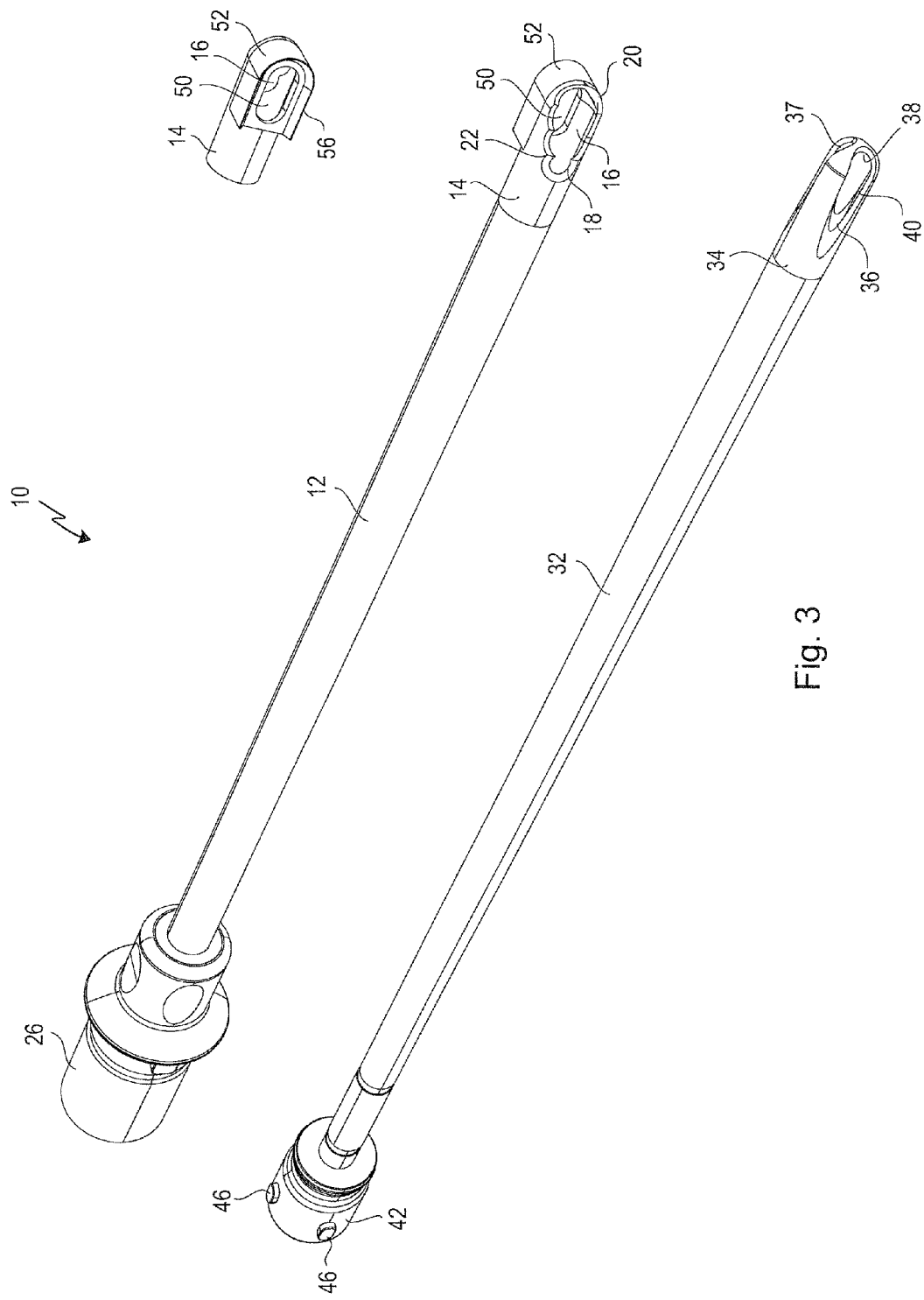
FIG. 3 shows a perspective exploded view, from distal to proximal, of the inner shaft and of the outer shaft removed therefrom, wherein the distal end of the outer shaft is shown in two positions rotated through 180° about the longitudinal axis, such that the first window in the outer shaft can be seen and, on the other hand, the further window that is surrounded by the curette can be seen.

The latter has, in the area of its distal end 14, a first window 16, as can be seen particularly from FIG. 3.

The single first window 16 has a circumferential border 18, which is designed as a cutting edge 20.

Figure 4:
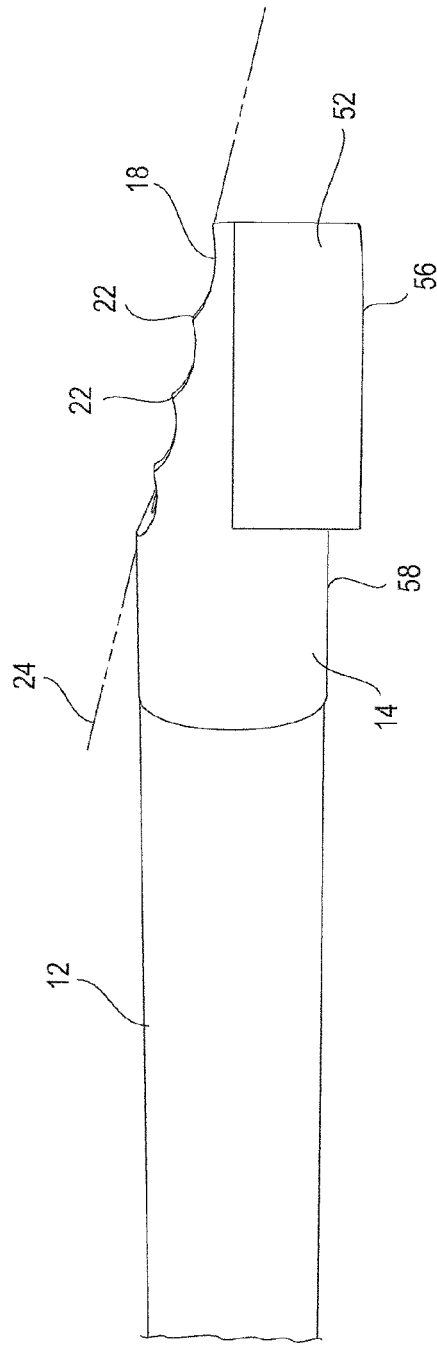
FIG. 4 shows a greatly enlarged side view, corresponding to the depiction in FIG. 1, of the distal end of the outer shaft without the inner shaft.
Figure 5:
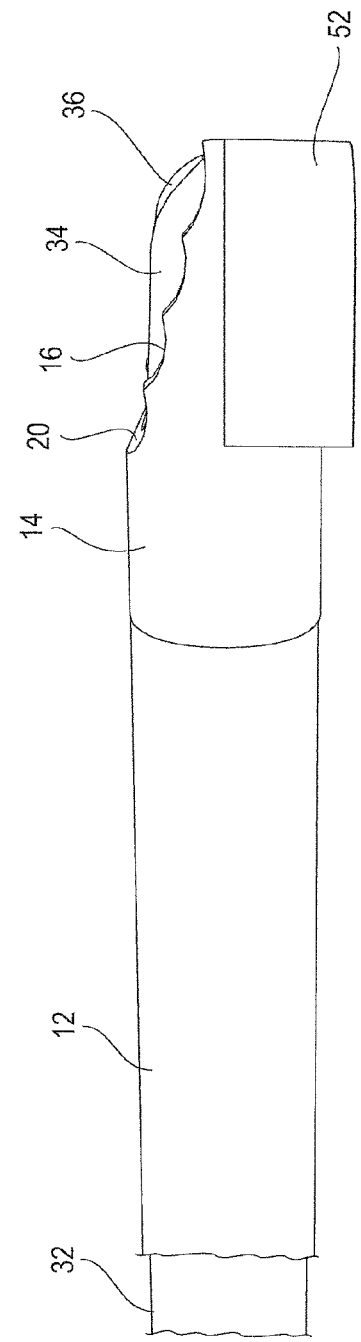
FIG. 5 shows a comparable view with the inner shaft inserted.

Teeth 22 stand vertically from the cutting edge 20, as can be seen particularly from FIGS. 3, 4 and 5.

The circumferential border 18 lies in the area of an oblique cut 24, as is indicated in FIG. 4. This oblique cut 24 is inclined radially inwards, as seen from proximal to distal, such that the first window 16 has an approximately oval cross section. As can be seen from FIG. 4, the inclination of the oblique cut 24 is such that less than half a diameter is cut away at the distal apex.

The teeth 22 can be worked by subsequent machining or even during preparation of the oblique cut.

An inner shaft 32 is received in the outer shaft 12.

The inner shaft 32 is likewise designed as an elongate hollow shaft, of which the external diameter corresponds approximately to the clear internal diameter of the outer shaft 12.

In the area of its distal end 34, the inner shaft 32 is provided on its circumference with three openings 36, 37, and 38 in an approximately uniform distribution.

Each of the openings 36, 37 and 38 is provided on its circumferential border with a peripheral cutting edge 40, wherein only the cutting edge 40 of the opening 36 is provided with a reference sign. The length of the inner shaft 32 is chosen such that it can be pushed completely into the outer shaft 12 from the proximal direction.

Figure 2:
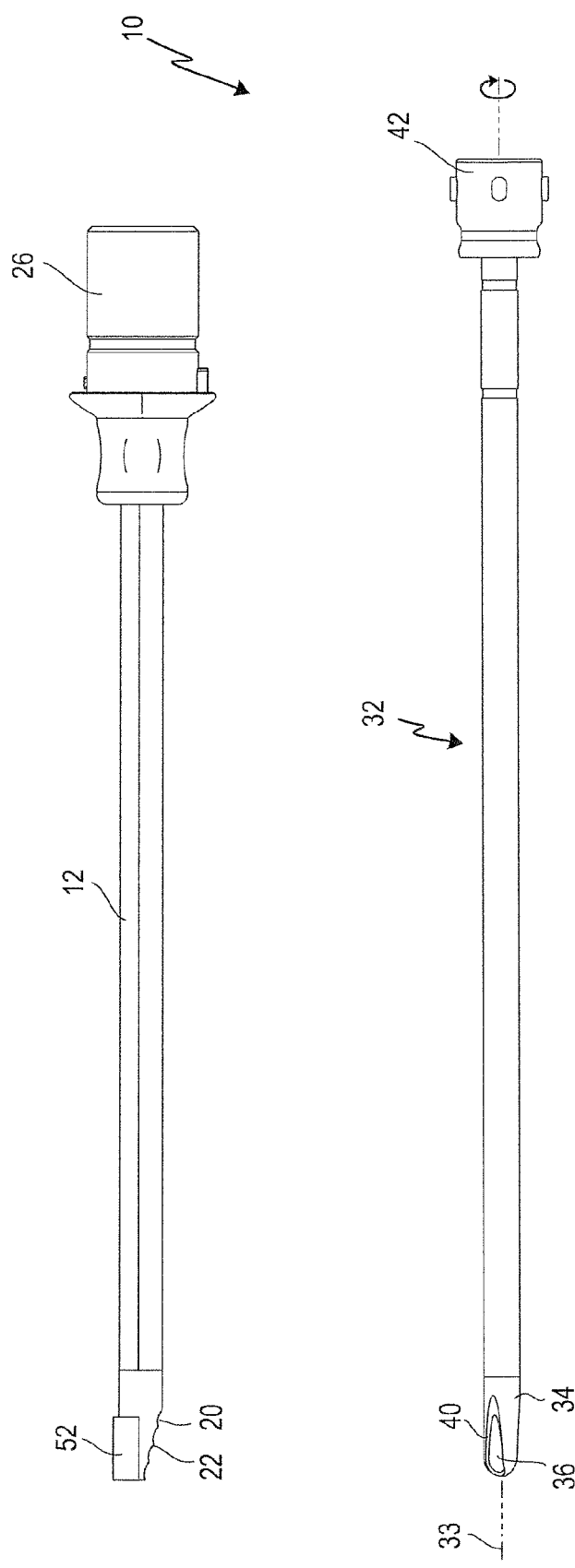
FIG. 2 shows a side view, comparable to the depiction of FIG. 1, but in an exploded representation, i.e. with the inner shaft removed from the outer shaft.

The three openings 36, 37 and 38 then lie at the level of the first window 16 in the outer shaft 12, as can be seen from the exploded view in FIG. 2. It will be seen from FIG. 5 that the distal end 34 of the inner shaft 32 protrudes with its openings slightly out from the first widow 16 in the lateral direction.

When the inner shaft 32 is rotated about its longitudinal axis 33, which is also at the same time the longitudinal axis of the instrument 10 and that of the outer shaft 12, the cutting edges 40 of the openings 36, etc., rotate too and run past the circumferential border 18, likewise designed as a cutting edge 20, of the first window 16 in the outer shaft 12. Scissor-like cuts then take place.

Figure 1:
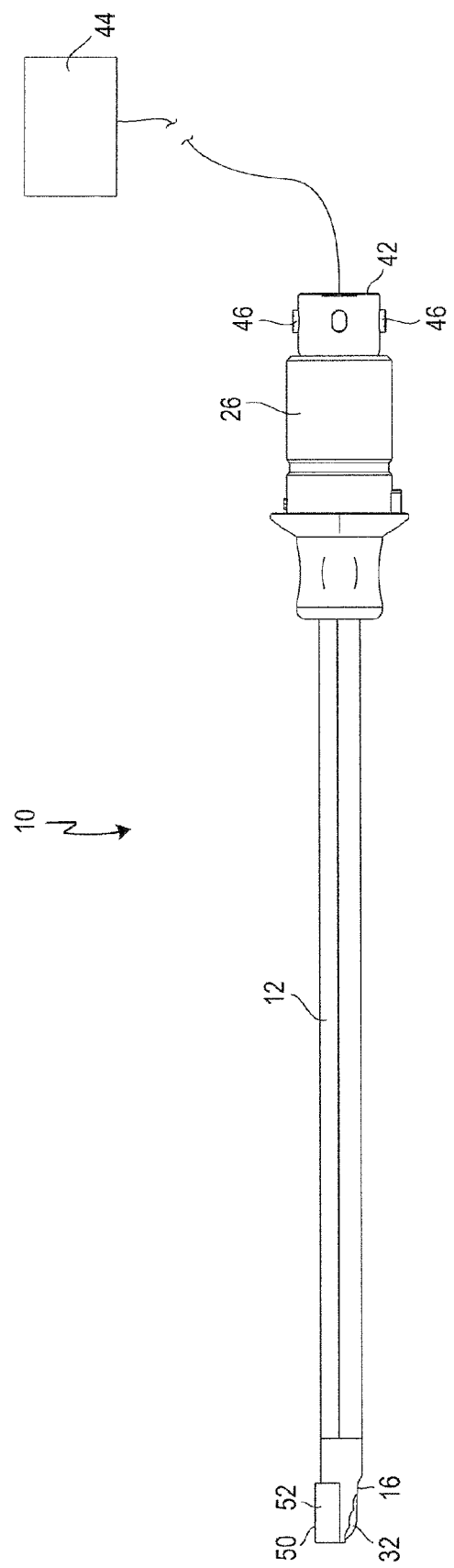
FIG. 1 shows a side view of a medical instrument according to the invention and indicates the attachment to a vacuum source.

At the proximal end, the inner shaft 32 has an attachment piece 42 via which the inner shaft 32 can be attached to a vacuum source 44, as is indicated in FIG. 1.

In addition, the attachment piece 42 also has radially protruding coupling pins 46 on which it is possible to place a coupling piece of a drive (not shown here) with which the inner shaft 32 can be rotated in the outer shaft 12. The proximal end of the outer shaft 12 is provided with a coupling piece 26.

The attachment piece 42 of the inner shaft 32 can be inserted and housed in the coupling piece 26 as shown in FIG. 1.

The coupling piece 26 holds and guides the inner shaft 32 within the outer shaft 12 via the attachment piece 42.

The attachment piece has an outer groove, into which groove an inner flange at the inner surface of the sleeve-like hollow coupling piece 26 can snap in when inserting the attachment piece 42 from proximal to distal into the coupling piece 26.

This area of the instrument 10 works as what is called a "shaver blade".

By virtue of the fact that the inner shaft 32 partially protrudes in the area of the first window 16 of the outer shaft 12, as is shown in FIG. 5, particularly aggressive cutting of tissue can be performed.

For this purpose, the circumferential border 18, which is provided with the teeth 22, is placed onto the tissue. When the inner shaft 32 is rotated, the cutting edges 40 of the openings 36, 37, 38, in conjunction with the cutting edge 20 of the first window 16 in the outer shaft, cut off corresponding pieces of tissue, and these are sucked into the interior of the inner shaft 32 through the openings 36, 37, 38 and carried off. The vacuum ensures that the tissue parts which are to be separated are sucked laterally onto the first window 16 in the outer shaft 12 and then separated.

On the side lying diametrically opposite to this "shaver blade" construction, a further approximately oval window 50 is cut out in the outer shaft 12, as can be seen in particular from FIGS. 3, 6 and 7.

This further window 50 is surrounded by a curette 52, which has the contour 54 of a U that is open in the proximal direction. The radially outer edge of the U is designed as a sharp separating edge 56. As can be seen in particular from FIG. 4, this separating edge 56 protrudes laterally from the outer face 58 of the outer shaft 12.

It will be seen from the perspective view in FIG. 6 that access to the interior of the outer shaft 12 is permitted via the further window 50.

It will be seen from FIG. 7 that, when the inner shaft 32 is pushed in, the openings 36, 37 and 38 also lie in the area of the further window 50.

If cartilage pieces, even relatively large cartilage pieces covering the complete area of the U, are now separated by the separating edge 56, these pieces are moved through the further window 50 in the direction of the interior of the outer shaft 12 and are fragmented into very small pieces by the rotating cutting edges 40 of the openings 36, 37 and 38 in the inner shaft. When these pieces are small enough, they can be sucked through the openings 36, 37 and 38 into the inner shaft 32 and carried off. For facilitating this cutting action, the inner edge of the further window 50 is designed as a cutting edge cooperating with the cutting edges 40 of the openings 36, 37 and 38.

When the curette 52 is placed with the separating edge 56 onto a cartilage area and is urged and has penetrated in the tissue or cartilage up to the depth of the bone, these separated cartilage areas are initially caught in the space "under" the curette 52 and cannot escape into the joint. When these relatively large cartilage pieces have then been fragmented into sufficiently small pieces, they can be sucked off through the inner shaft 32.

The separating edge 56 can also be designed as a closed edge extending in an oval shape around the oval window 50. The area surrounded by the separating edge is always larger than the area of the openings in the inner shaft.

In the illustrative embodiment shown, this separating edge 56 is open in the proximal direction.

This makes it easier for the person handling the instrument 10 to place the curette 52 on a defect site.

Thus, for example, the operator can first of all push the distally closed area of the separating edge 56 onto the defect site and position it such that it comes to lie slightly behind the area of the defect site furthest from the operator and encloses this area. He can then gradually urge the separating edge 56 into the cartilage tissue. He can observe this at least partially through the proximally open end 59 of the profile.

Figure 8:
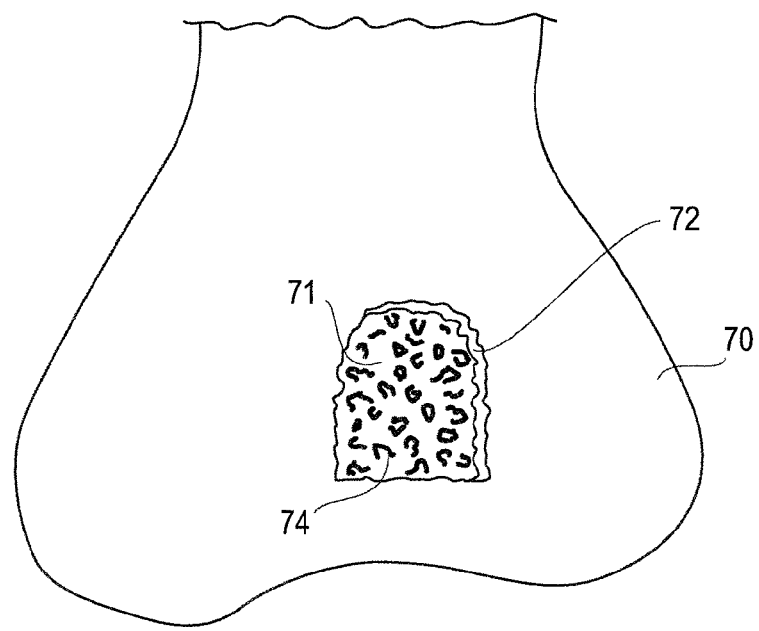
FIG. 8 shows a highly schematic view of a femoral bone in the area of the knee joint with a defect site, after the latter has been treated by the shaver blade area of the instrument.

FIG. 8 is a highly schematic representation of a femoral bone 70 in the area of a knee joint.

A defect 71 was present there, which has been initially treated using the "shaver blade" of the instrument 10. In the area of the defect 71, a relatively undefined circumferential margin 72 forms on the surrounding tissue of the bone 70. The bone substance 74 is already exposed.

Figure 9:
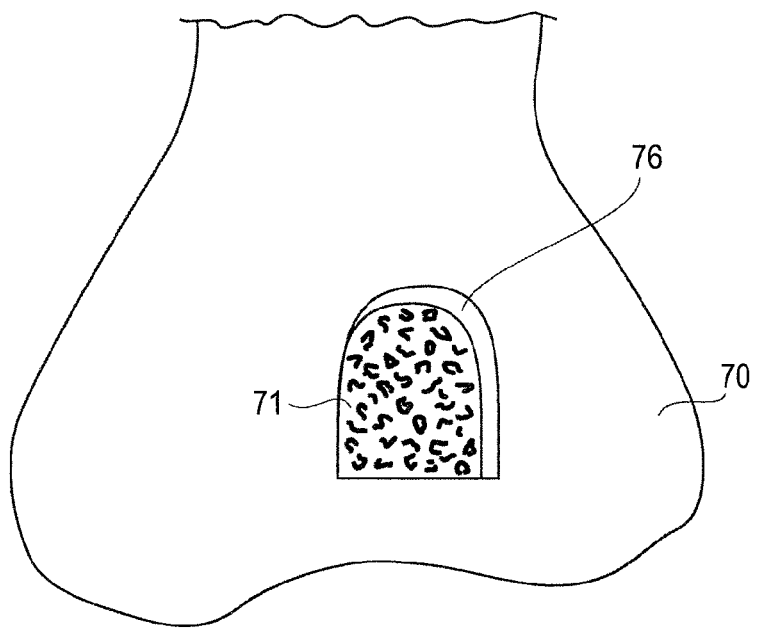
FIG. 9 shows the situation after the defect site has been worked using the curette.

FIG. 9 now shows the defect 71 after the curette 52 has been applied and urged in and the cartilage tissue at the margin has been removed down to the bone substance 74.

The smooth and sharp separating edge 56 of the curette 52 has resulted in a defined margin 76 which corresponds to the geometry of the latter and which stands approximately at right angles from the bone surface.

This is the aim of a successful preparation of a defect site onto which a suitably fashioned graft is intended to be placed. This smooth margin 76, standing approximately at right angles, is a decisive factor in providing immediate, firm and transition-free fusion of an implant. After a certain period of time, the defect 71 is completely closed without scarring. The substantial loads that act in this area, particularly in a knee joint, can then be supported again.

As has already been mentioned, the contour 54 of the separating edge 56 of the curette can also be closed, oval or round. The surface of the separating edge can also extend in a suitable curvature if such defects occur on extremely curved bone sites, such that the contour of the curette, or of the separating edge 56 thereof, can then already be adapted to this bone contour.

The invention claimed is:

1. A medical instrument for cutting off tissue and cartilage from a body, comprising
   an outer shaft having a distal end and a proximal end, and having a longitudinal axis,
   said outer shaft having at least a one first window in an area of said distal end, each of said at least one first window having at least one cutting edge;
   a hollow inner shaft received in said outer shaft,
   said hollow inner shaft being rotatable about said longitudinal axis, wherein a proximal end of said hollow inner shaft is attachable to a vacuum source,
   said hollow inner shaft having, at its distal end area, at least one opening comprising at least one cutting edge cooperating with at least one of said at least one cutting edge of said at least one first window of said outer shaft in a cutting action when turning said hollow inner shaft, thereby cutting off tissue and cartilage from the body, and
   wherein one further window is provided in said distal end area of said outer shaft,
   said further window being surrounded by a curette having a separating edge for separating tissue and cartilage from said body by penetrating said separating edge thereinto,
   wherein said further window is in an area of said at least one opening of said hollow inner shaft allowing to cut tissue and cartilage separated by said separating edge of said curette into small pieces that are adapted to be sucked in through said at least one opening in said hollow inner shaft,
   wherein said separating edge of said curette lies in one plane, and
   wherein said separating edge of said curette is disposed on a protruding portion that protrudes radially away from an outer surface of said outer shaft, a height of said curette corresponding at least to a thickness of a layer of tissue or cartilage that is to be removed.

2. The medical instrument of claim 1, wherein a contour of said separating edge of said curette is U-shaped when said outer shaft is viewed radially from an outside.

3. The medical instrument of claim 2, wherein an open end of said U-shaped contour lies at a proximal side of said curette.

4. The medical instrument of claim 1, wherein said outer shaft has a single first window arranged diametrically opposite to said further window surrounded by the separating edge of said curette.

5. The medical instrument of claim 1 wherein one of said at least one first window in said outer shaft is formed by an oblique cut of said outer shaft, said oblique cut being inclined radially inwards to said longitudinal axis seen from proximal to distal.

6. The medical instrument of claim 5, wherein said inner shaft protrudes from one of said at least one first window in an area of said oblique cut.

7. The medical instrument of claim 1, wherein a circumferential border of one of said at least one first window in said outer shaft has teeth standing vertically upwards from said circumferential border.

8. The medical instrument of claim 1, wherein said at least one opening of said rotatable hollow inner shaft has a plurality of openings.

9. The medical instrument of claim 8, wherein said plurality of openings in said inner shaft are distributed circumferentially about said inner shaft.

10. The medical instrument of claim 1, wherein said at least one opening of said hollow inner shaft has three openings.

11. The medical instrument of claim 1, wherein said outer shaft has, at its proximal end, a coupling piece for coupling and guiding said inner shaft in said outer shaft.

12. The medical instrument of claim 1, wherein said inner shaft has, at its proximal end, an attachment piece to which a vacuum source is connectable.

13. The medical instrument of claim 12, wherein said attachment piece is coupleable via coupling elements to a drive which rotates said inner shaft about said longitudinal axis relative to said stationary outer shaft.

* * * * *